United States Patent
Aoki et al.

(10) Patent No.: US 7,705,302 B2
(45) Date of Patent: Apr. 27, 2010

(54) SCANNING ELECTRON MICROSCOPE

(75) Inventors: Yasuko Aoki, Hitachi (JP); Tetsuya Sawahata, Hitachinaka (JP); Mine Araki, Hitachinaka (JP); Atsushi Muto, Hitachinaka (JP); Shuichi Takeuchi, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 260 days.

(21) Appl. No.: 12/021,810

(22) Filed: Jan. 29, 2008

(65) Prior Publication Data

US 2008/0191135 A1 Aug. 14, 2008

(30) Foreign Application Priority Data

Jan. 30, 2007 (JP) .............................. 2007-018654

(51) Int. Cl.
 H01J 37/28 (2006.01)
 H01J 37/26 (2006.01)
 G01N 23/00 (2006.01)

(52) U.S. Cl. .................. 250/310; 250/311; 250/306; 250/307; 250/396 R; 250/397

(58) Field of Classification Search ................. 250/310, 250/311, 306, 307, 396 R, 397
See application file for complete search history.

(56) References Cited

U.S. PATENT DOCUMENTS

| | | | |
|---|---|---|---|
| 4,897,545 A | | 1/1990 | Danilatos |
| 5,608,218 A | * | 3/1997 | Sato et al. .................. 250/310 |
| 5,644,132 A | | 7/1997 | Litman et al. |
| 5,872,358 A | * | 2/1999 | Todokoro et al. ............ 250/310 |
| 6,501,077 B1 | | 12/2002 | Sawahata et al. |
| 6,633,034 B1 | * | 10/2003 | Crewe .......................... 850/9 |
| 6,642,520 B2 | | 11/2003 | Kimura et al. |
| 6,710,340 B2 | * | 3/2004 | Kazumori ...................... 850/9 |
| 2003/0150991 A1 | | 8/2003 | Kazumori |
| 2004/0245465 A1 | | 12/2004 | Steigerwald et al. |
| 2007/0120071 A1 | | 5/2007 | Steigerwald et al. |

FOREIGN PATENT DOCUMENTS

| | | |
|---|---|---|
| EP | 0 721 201 A1 | 7/1996 |
| JP | 4-504325 T2 | 7/1992 |
| JP | 8-273569 A | 10/1996 |
| JP | 9-171791 A | 6/1997 |

(Continued)

OTHER PUBLICATIONS

Abstract of JP9507331T, Jul. 22, 2007 Metrologix Inc. corresponds to B6.

(Continued)

Primary Examiner—Nikita Wells
(74) Attorney, Agent, or Firm—Crowell & Moring LLP

(57) ABSTRACT

An object of the present invention is to provide a scanning electron microscope including decelerating-electric-field forming means for decreasing the energy of a beam of electrons reaching a sample, and being capable of selectively detecting BSEs with high efficiency. To this end, the scanning electron microscope including the decelerating-electric-field forming means has a detector for detecting electrons. The detector includes a part for receiving the electrons at a position which is positioned outside trajectories of SEs accelerated by the decelerating-electric-field forming means, and which is further away from the optical axis of the beam of electrons than the trajectories of the SEs.

12 Claims, 7 Drawing Sheets

FOREIGN PATENT DOCUMENTS

| | | |
|---|---|---|
| JP | 11-273808 A2 | 10/1999 |
| JP | 2000-299078 A2 | 10/2000 |
| JP | 2002-324510 A | 11/2002 |
| JP | 2004-221089 A | 8/2004 |
| WO | WO 95/12210 A1 | 5/1995 |
| WO | WO 00/19482 A1 | 4/2000 |

OTHER PUBLICATIONS

Abstract for Japanese Patent No. 09171791A2 listed as document B7 filed on Jan. 29, 2008.

* cited by examiner

SCANNING ELECTRON MICROSCOPE

CLAIM OF PRIORITY

The present application claims priority from Japanese application JP 2007-18654 filed on Jan. 30, 2007, the content of which is hereby incorporated by reference into this application.

BACKGROUND OF THE INVENTION

1. Field of the Invention

The present invention relates to a scanning electron microscope which scans a beam of electrons on a sample, and detects electrons emitted from the scanning spot. Particularly, the present invention relates to a scanning electron microscope which includes decelerating-electric-field forming means for reducing the energy reaching the sample, and which is suitable for detecting backscattered electrons or secondary electrons emitted from the scanning spot.

2. Description of Related Art

A scanning electron microscope forms an image of a sample in accordance with the following scheme. The scanning electron microscope accelerates electrons emitted from a source of electrons, and thereafter focuses electrons by use of an electrostatic lens or an electromagnetic lens, thus turning the focused electrons into a narrowly-focused beam of electrons (a primary beam of electrons). Hence, the scanning electron microscope scans the beam of electron on a sample, and thereby detects electrons emitted from the sample, hence displaying the strength of the signal thus detected On a displaying apparatus in synchronism with the scanning of the beam of electrons.

The electrons emitted from the sample by irradiating the beam of electrons on the sample have a wide energy distribution. Parts of the primary beam of electrons irradiated on the sample are elastically scattered by atoms positioned in the surface of the sample. These are termed as backscattered electrons (hereinafter shortened to "BSEs", and also hereinafter referred to as "reflected electrons" in some cases). It is known that most of the BSEs has the same level of energy as the beam of electrons.

In addition, other parts of the beam of electrons interact with atoms positioned inside the sample. As a result, electrons positioned inside the sample receive kinetic energy, and thus are emitted from the sample. These are termed as secondary electrons (hereinafter shortened to "SEs"). It is known that most of the SEs has an energy of less or equal to 50 eV, or of approximately 10 eV on the average.

Out of the electrons emitted from the sample, the BSEs carry information on the composition of the sample. While, the scanning electron microscope is required to meet needs for doing such as analyzing the composition by selectively detecting the BSEs. Scanning electron microscopes which selectively detect BSEs or distinguish BSEs from SEs are described respectively in Japanese Patent Application Laid-open Publication No. 2004-221089 (hereinafter referred to as "Patent Document 1)," Japanese Paten Application Laid-open Publication No. 2002-324510 (hereinafter referred to as "Patent Document 2)," International Publication No. WO00/19482 (hereinafter referred to as "Patent Document 3)," Japanese Patent Application Laid-open Publication No. Hei 8-273569 (hereinafter referred to as "Patent Document 4)".

Patent Document 1 describes a configuration of the scanning electron microscope which has a aperture arranged in a vicinity of the crossover of BSEs and has a detector arranged between the aperture and the source of electrons, as well as which thus detects a signal in the center of the BSE.

Patent Document 2 describes a configuration of the scanning electron microscope which has a detector arranged off the optical axis of the beam of electrons, and which thus applies a positive voltage of approximately 10 kV to a vicinity of the detector in order to guide secondary electrons.

This configuration guides the SEs to the detector due to the strong electric field. However, the trajectories of BSEs are not bent so much because of their high energy. As a result, the BSEs travel straight toward the source of electrons.

Patent Document 3 describes a configuration of the scanning electron microscope which has a secondary electron conversion electrode in the trajectories of BSEs, and which switches between the detection of SEs and the detection of BSEs by doing such as changing voltages applied to the secondary electron conversion electrode. Here, the trajectories of BSEs are changed by an electromagnetic objective lens.

Patent Document 4 describes a technology which causes the scanning electron microscope to separate the trajectories of SEs from the trajectories of the BSEs by use of the focusing effect of each corresponding lens, as well as which detects the BSEs by use of a BSE detector arranged inside the optical axis of the beam of electrons, and detects the SEs by use of a SE detector arranged outside the optical axis of the beam of electrons.

Japanese Patent Translation Publication No. Hei 9-507331 (hereinafter referred to as "Patent Document 5) describes a technology which decelerates the landing energy of a beam of electrons (or an energy which the beam of electrons has when reaching a sample) by applying a negative voltage to the sample. In addition, this patent document describes a technology to selectively detect BSEs by use of a detector which is arranged above the objective lens (closer to the source of electrons). Because a negative voltage is applied to the detector for detecting BSEs, SEs are repulsed back to the sample due to their lower energy than that of the BSEs. As a result, the BSEs are selectively detected.

Japanese Patent Application Laid-open Publication No. Hei 9-171791. (hereinafter referred to as "Patent Document 6) also describes a technology which decelerates the landing energy of a beam of electrons by applying a negative voltage to the sample (this technology is sometimes termed as a retarding technology). This technology makes it possible to decrease the energy of the beam of electrons which reaches the sample, with the energy of the beam of electrons kept at a high level while the beam of electrons passing the object lens. This enables the scanning electron microscope to have a higher resolution, and to cause less damage on the sample, at the same time.

SUMMARY OF THE INVENTION

The technologies disclosed by Patent Documents 1 to 5 enable their respective scanning electron microscopes to selectively detect SEs or BSEs, or to detect SEs and BSEs in a synthetic manner. However, these technologies have their own problems as follows.

The technology disclosed in Patent Document 1 causes the aperture to be arranged in the crossover of the BSEs, and thus separates the BSEs passing the aperture from the other electrons colliding against the aperture. However, the direction in which the BSEs are emitted ranges wide, and BSEs emitted out of the aperture angle of the beam of electrons is large in amount. A convergent point of BSEs emitted at an angle away from the optical axis of the beam of electrons is different from that of BSEs emitted at an angle along the optical axis of the beam of electrons. This reduces the amount of BSEs selectively detected when a aperture with a smaller diameter is used.

On the other hand, if a aperture with a larger diameter is used for the purpose of compensating for the reduction in the detection efficiency, this use allows the SEs to pass the aperture. This obstructs the initial objective of selectively detecting BSEs.

Patent Documents 2 and 3 disclose that the trajectories of the SEs are separated from those of the BSEs by use of the electric field effect and the magnetic field effect. If the retarding technology described in Patent Document 6 is adopted for the technologies disclosed in Patent Documents 2 and 3, the SEs are highly accelerated. This brings about a problem that it is difficult to separate the trajectories of the SEs from those of the BSEs by use of the difference in energy level between the SEs and the BSEs, and that it is difficult to detect the SEs and the BSEs while separating the SEs from the BSEs.

Although Patent Document 4 describes the technology for separating the SEs and the BSEs by the convergent effect of each corresponding lens, an experiment conducted by the inventors did not show that the trajectories of the SEs passed outside the trajectories of the BSEs, Particularly in a case where the electrostatic lens (for example, the retarding technology and the like) is used, the velocity of electrons emitted from the sample is equal to a value obtained by superimposing the initial vector of the electrons on a vector of the electrons accelerated by the electrostatic lens. This compresses the distribution of angles at which the electrons travel.

Particularly, the SEs are influenced by the acceleration vector caused by the electrostatic lens. For this reason, the SEs do not travel largely away from the optical axis of the beam of electrons before decelerated. For example, in a case where the SEs had the kinetic energy of 10 eV while the potential difference formed by the electrostatic lens was set at 1500V, the inventors were able to calculate from the addition of a velocity vector that SEs, scattered at a direction perpendicular to the optical axis of the beam of electrons, traveled at an angle of 0.4 degrees to the beam of electrons at a time point when the SEs thus scattered passed the electrostatic lens.

In other words, the arrangement of the detector which is described in Patent Document 4 brings about a problem that it is difficult to detect the SEs and the BSEs while separating the SEs and the BSEs, because the SEs passes in a very narrow angle range about the optical axis of the beam of electrons.

Patent Document 5 describes a technology for causing the scanning electron microscope to negatively bias the detecting surface of the detector, and to detect BSEs which pass their trajectories closer to the optical axis of the beam of electrons, and which are emitted at a relatively high angle.

Because, however, a voltage equal to the voltage applied to the sample needs to be applied to the detecting surface, it is likely that the electric field, formed while applying the voltage to the detecting surface, may adversely affect the trajectories of the beam of electrons passing a vicinity of the electric field. As a countermeasure against the adverse affect, it is conceivable that a shielding member for blocking the leakage of the electric field is arranged between the detecting surface of the detector and the trajectories of the beam of electrons. However, the detecting surface needs to be constructed in a smaller scale in order to secure a space for providing the shielding member there. This brings about a problem that the detection efficiency is decreased, and a problem that the structure of the scanning electron microscope becomes complicated.

An object of the present invention is to provide a scanning electron microscope which includes decelerating-electric-field forming means for reducing the energy reaching the sample, and which is capable of selectively detecting BSEs or SEs with high efficiency.

A first aspect of the present invention for the purpose of achieving the object causes a scanning electron microscope having decelerating-electric-field forming means to include a detector for detecting electrons. The detector is configured in order that its electron receiving part is provided at a position which is outside the trajectories of SEs accelerated by the decelerating-electric-field forming means, as well as which is further away from the optical axis of the beam of electrons than the trajectories of the SEs.

Because the decelerating electric field thus formed converges the SEs on a vicinity of the optical axis of the electron beams, the arrangement of the detector including its part for selectively receiving BSEs passing their trajectories outside the trajectories of the SEs makes it possible for the scanning electron microscope to selectively detect the BSEs with high efficiency.

The decelerating-electric-field forming technology can make the resolution of the apparatus higher, while the technology brings about a problem that the trajectories of the SEs are converged on the vicinity of the optical axis. Because the amount of signal in the SEs is larger than that in the BSEs, it is likely that information on the BSEs may be lost when SEs converged on a spot is detected.

The first aspect of the present invention makes use of a phenomenon in which the SEs are converged on the vicinity of the optical axis whereas the BSEs pass their trajectories positioned outside the SEs, and thus selectively detects the BSEs which pass their trajectories positioned outside the trajectories which the converged SEs pass. This enables the scanning electron microscope to selectively detect the BSEs with high efficiency.

Another aspect of the present invention causes a scanning electron microscope having decelerating-electric-field forming means to include multiple parts each for receiving electrons emitted from a sample, and to include a mechanism for selecting the parts each for receiving electrons for use depending on the types of electrons to be detected.

As described above, the scanning electron microscope having the decelerating-electric-field forming means has a tendency to converge the SEs on the optical axis of the beam of electrons. The purpose of detecting the BSEs with a higher efficiency, while preventing the detection from being obstructed by the information on the SEs, can be achieved by the arrangement of the detector including the parts each for selectively receiving BSEs passing their trajectories positioned outside the trajectories which the converged SEs pass.

In the apparatus having the configuration which enables the BSEs to be selectively detected, a part for receiving SEs is arranged closer to the inside than the part for receiving the BSEs, for the purpose of detecting the SEs. Such configuration enables the scanning electron microscope to detect SEs, which are converged on the vicinity of the optical axis by the decelerating electric field, with high efficiency. In addition, this configuration is capable of making smaller the surfaces each for receiving SEs, whereas the configuration makes larger the area in which BSEs are capable of being detected. This enables the scanning electron microscope to detect the BSEs, which has the smaller amount of signal than the SEs has, with high efficiency.

One aspect of the present invention enables the scanning electron microscope including the decelerating-electric-field forming means to selectively detect the BSEs with high efficiency. In addition, another aspect of the present invention enables the scanning electron microscope including the decelerating-field-field forming means to switch between the detection of the BSEs and the detection of the SEs depending on the necessity, and to selectively detect the BSEs and/or the SEs with high efficiency.

BRIEF DESCRIPTIONS OF THE DRAWINGS

DESCRIPTION OF THE PREFERRED EMBODIMENTS

Figure 1:
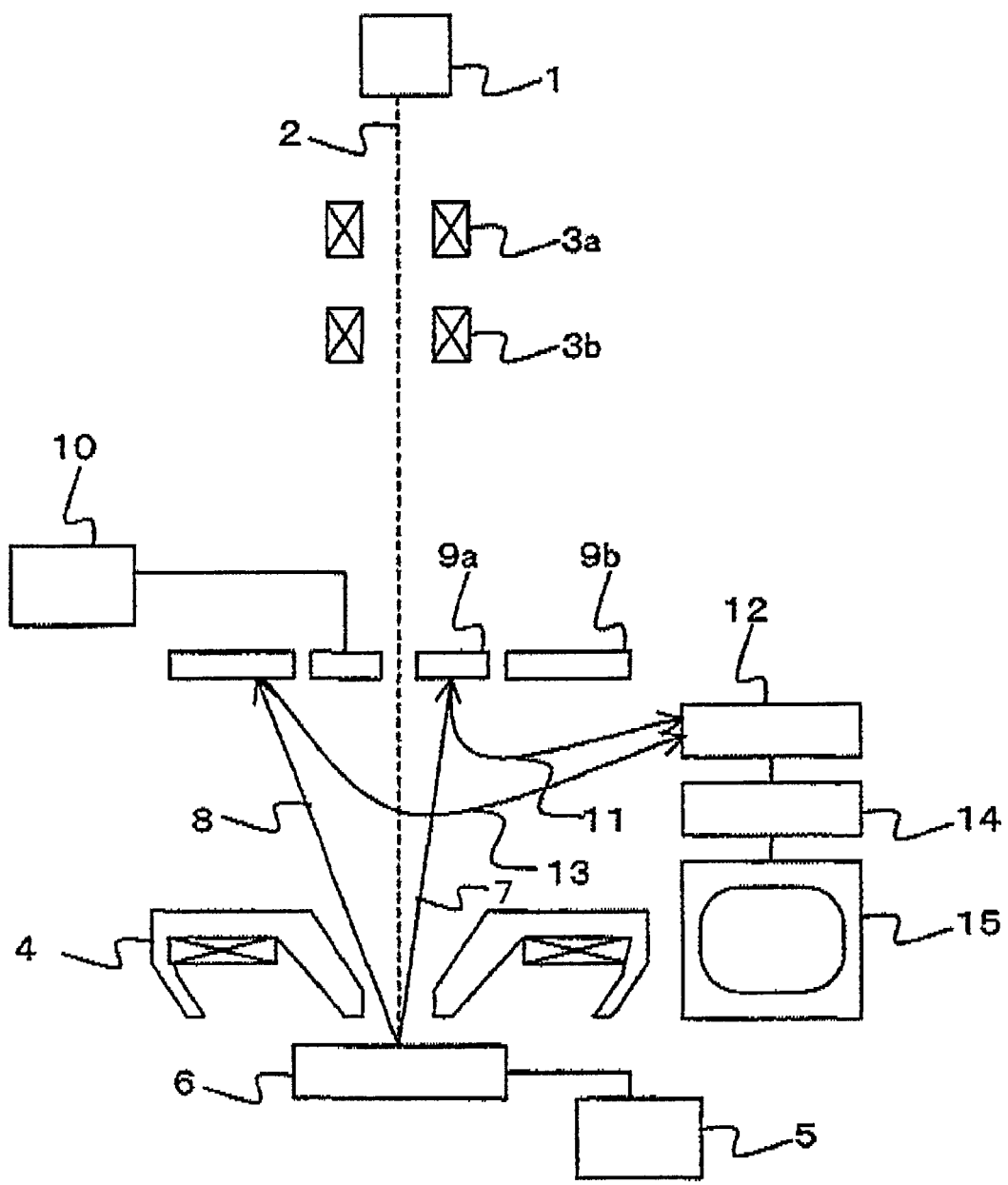
FIG. 1 is a diagram for explaining an example of a scanning electron microscope.

FIG. 1 is a diagram for schematically explaining a scanning electron microscope, and particularly for explaining a configuration thereof which uses an objective lens (semi-in lens whose lens gap is opened downward (toward a sample)).

FIG. 1 is a diagram for an example of a scanning electron microscope additionally employing a deceleration method of decelerating a primary beam of electrons between the objective lens and the sample by applying a negative voltage to the sample. The scanning electron microscope includes an inner annular electrode plate and an outer annular electrode plate, about the optical axis of the primary beam of electrons; and a detector arranged at a position shifted from the optical axis of the primary beam of electrons. The inner and outer electrode plates as well as the detector are positioned near the objective lens, and on the side of a source of electrons. The scanning electron microscope additionally includes a mechanism for changing voltage applied to the inner electrode plate. Although the scanning electron microscope of the present example is configured by including the semi-in objective lens, a lens in shape other than the semi-in lens brings about the same effect as the semi-in lens.

A primary beam of electrons 2 (hereinafter referred to as a "beam of electrons") emitted from a source of electrons 1 is scanned by deflectors 3a and 3b arranged in two tiers, and is thus focused on the sample by an objective lens 4. A decelerating-voltage applying voltage supply 5 applies a negative voltage to a sample 6 via a sample stage, which is not illustrated. The decelerated electric field additionally functions as an electrostatic lens. For this reason, the primary beam of electrons 2 is focused on the sample 6 due to an effect of superimposing the magnetic field caused by the objective lens 4 on the electric field and generated by the decelerating-voltage applying voltage supply 5.

In addition, the objective lens is set at the ground potential. For this reason, the primary beam of electrons 2 is decelerated by the electric field which the decelerating-voltage applying voltage supply 5 causes between the objective lens and the sample, and is thus irradiated on the sample at a speed lower than that at which the primary beam of electrodes passes the objective lens.

The irradiating of the primary beam of electrons 2 on the sample 6 causes secondary electrons 7 and reflected electrons 8 to be emitted from the sample 6. The secondary electrons 7 have an energy of equal to or less than 50 eV, or an energy of approximately 10 eV on the average. The scattered intensity distribution is in proportion with cos θ. θ denotes an angle of the secondary beam of electrons thus emitted to a line perpendicular to the surface of the sample (or the optical axis of the beam of electrons). The secondary electrons 7 are accelerated by the electric field caused between the objective lens and the sample. In the case of the scanning electron microscope of the present example, the voltage applied to the sample by the decelerating-voltage applying voltage supply 5 is set at −1500V. However, no matter how the applied voltage is changed, the voltage brings about the same effect.

The secondary electrons 7 have an energy of 1500 eV to 1550 eV, or an energy of approximately 1510 eV on the average. The secondary electrons 7 are guided upward of the objective lens. At this time, the velocity of the secondary electrons 7 is that obtained by adding the velocity of secondary electrons accelerated by the electric field caused between the objective lens and the sample along the optical axis of the beam of electrons to the velocity of secondary electrons generated on the sample. As a result, the velocity component in a direction perpendicular to the optical axis of the beam of electrons maintains only the velocity component in the direction perpendicular to the optical axis of the beam of electrons out of the velocity of the secondary electrons which are generated on the sample. As a result, the average of the velocity component corresponds to an energy of approximately 10 eV at maximum.

The maximum aperture angle caused by the velocity addition is 0.4 degrees in the scanning electron microscope of the present example. The secondary electrons travel while receiving a force as a whole in the convergent direction due to the magnetic field generated by the objective lens 4, and thus reach the detection electrode 9. Descriptions will be provided for a case where a member for detecting BSEs is arranged outside the trajectories of the SEs (outward when viewed from the optical axis of the beam of electrons (from the idealistic trajectory which the beam of electrons passes when not deflected)).

The detection electrode 9 is configured of an inner annular part 9a and an outer annular part 9b, and is that for receiving electrons emitted from the sample 6. The scanning electron microscope of the present example will be described citing a case where a secondary electron conversion electrode, which generates secondary electrons by the collision of electrons, is adopted as the detection electrode 9. What can be adopted as the detection electrode 9 is not limited to the secondary electron conversion electrode. For example, the detecting surface of a multi-channel plate (or a member for amplifying an electron signal) may be arranged directly.

The inner annular part 9a and the outer annular part 9b are electrically insulated from each other, and are each formed in the shape of a circle. The outer annular part 9b is grounded. A voltage applying mechanism 10 is electrically connected to the inner annular part 9a, and is thus capable of applying an arbitrary voltage to the inner annular part 9a. A hole is made in a center portion of the inner annular part 9a in order that the beam of electrons 2 can pass the hole. The velocity component of the secondary electrons in the direction perpendicular to the optical axis of the beam of electrons is small, so that the secondary electrons collide against the inner annular part 9a without traveling largely away from the optical axis of the beam of electrons. The inner annular part 9a is arranged in the trajectories of the SEs, or on a line extending in a direction in which the trajectories of SEs passing the objective lens run. On the other hand, the outer annular part 9b is arranged in the trajectories of the BSEs, or on a line extending in a direction in which the trajectories of BSEs passing the objective lens run.

In addition, the inner annular part 9a includes: a part for receiving SEs; and an opening which the beam of electrons passes. The passage openings is are formed as an opening which is as small as possible to an extent of not obstructing the passage of the beam of electrons for the purpose of detecting SEs passing their trajectories close to the optical axis with high efficiency. The outer annular part 9b also includes an opening which the beam of electrons passes. The opening is made smaller than the opening made in the inner annular part 9a, which the beam of electrons passes.

When an image is intended to be obtained by use of both the secondary electrons and the reflected electrons, a ground potential or a negative potential of approximately −10V is supplied to the inner annular part 9a from the voltage applying mechanism 10. The energy of the secondary electrons colliding against the inner annular part 9a is as sufficiently large as 1500 eV to 1550 eV. As a result, secondary electrons 11 which are regenerated in the surface of the inner annular part 9a are emitted therefrom.

The inner annular part 9a is set as the ground potential or the negative potential, whereas the outer annular part 9b thereof and components (not illustrated) in its vicinity are set at the ground potential. For this reason, the secondary electrons are emitted from the surface of the inner annular part 9a. A secondary electron detector 12 is arranged at a position shifted from the optical axis of the beam of electrons. A voltage applying mechanism (not illustrated) is electrically connected to the front of the secondary electron detector 12, and applies a high voltage thereto. An electric field caused by this high voltage attracts the secondary electrons 11 thus regenerated, and a signal due to secondary electrons 7 is detected by the secondary electron detector 12.

In the case of the scanning electron microscope of the present example, the outer annular part 9b is arranged near the secondary electron detector 12, and on the side of the source of electrons. This arrangement enables the scanning electron microscope to detect BSEs which are emitted at a high angle around the optical axis of the beam of electrons. In addition, it is desirable that the inner annular part 9a and the outer annular part 9b should be arranged at the same height. If the two annular parts are arranged at different heights, this causes electrons which pass an interstice between the inner annular part 9a and the outer annular part 9b. For this reason, it is desirable from a viewpoint of detection efficiency that the two annular parts should be arranged at the same height. Moreover, from a viewpoint of making the working distance as short as possible, the inner annular part 9a and the outer annular part 9b are arranged near the objective lens 4, and on the side of the source of electrons 1.

The reflected electrons 8 have an energy almost equal to that which the primary beam of electrons has when irradiated on the sample. In the case of the scanning electron microscope of the present example, the irradiation voltage is set at 800 eV. However, no matter how the irradiation voltage is changed, the effect of the invention remains unchanged. Like the secondary electrons, the reflected electrons 8 are accelerated by the electric field generated between the objective lens and the sample. As a result, the reflected electrons 8 has an energy of 2300 eV, and is thus guided upward of the objective lens.

The maximum aperture angle caused by the velocity addition is 20.4 degrees in the present example. The velocity component of the velocity of the reflected electrons in the direction perpendicular to the optical axis of the beam of electrons is a speed corresponding to 800 eV at maximum, the secondary electrons travel while receiving a force as a whole in the convergent direction due to the magnetic field generated by the objective lens 4, and thus reach the detection electrode 9. Because the velocity component of the reflected electrons in the direction perpendicular to the optical axis of the beam of electrons is large, most of the reflected electrons collide against the outer annular part 9b although the rest of the reflected electrons collide against the inner annular part 9a.

Secondary electrons 13 are regenerated in each surface of the inner annular part 9a and the outer annular part 9b, and are emitted from the two annular parts due to the energy of the reflected electrons colliding against the two annular parts. The secondary electrons 13 thus regenerated are attracted by an electric field, which is caused due to the voltage applied to the front of the secondary electron detector 12, and hence reach the secondary electron detector 12. Thereby, a signal due to the reflected electrons 8 is detected by the secondary electron detector 12.

The signal detected by the secondary electron detector 12 and signals from the other detectors (not illustrated) are selected, combined and colored by signal processing means 14, followed by a display on a display device 15.

Specifically, in a case where the negative potential is supplied to the inner annular part 9a, both information on the secondary electrons 7 and information on the reflected electrons 8 are acquired at the same time. Because the amount of the secondary electrons 7 thus generated is larger than that of the reflected electrons 8 thus generated, an image to be obtained includes the information on the secondary electrons more than the information on the reflected electrons in the case where the two pieces of information are acquired at the same time.

Figure 2:
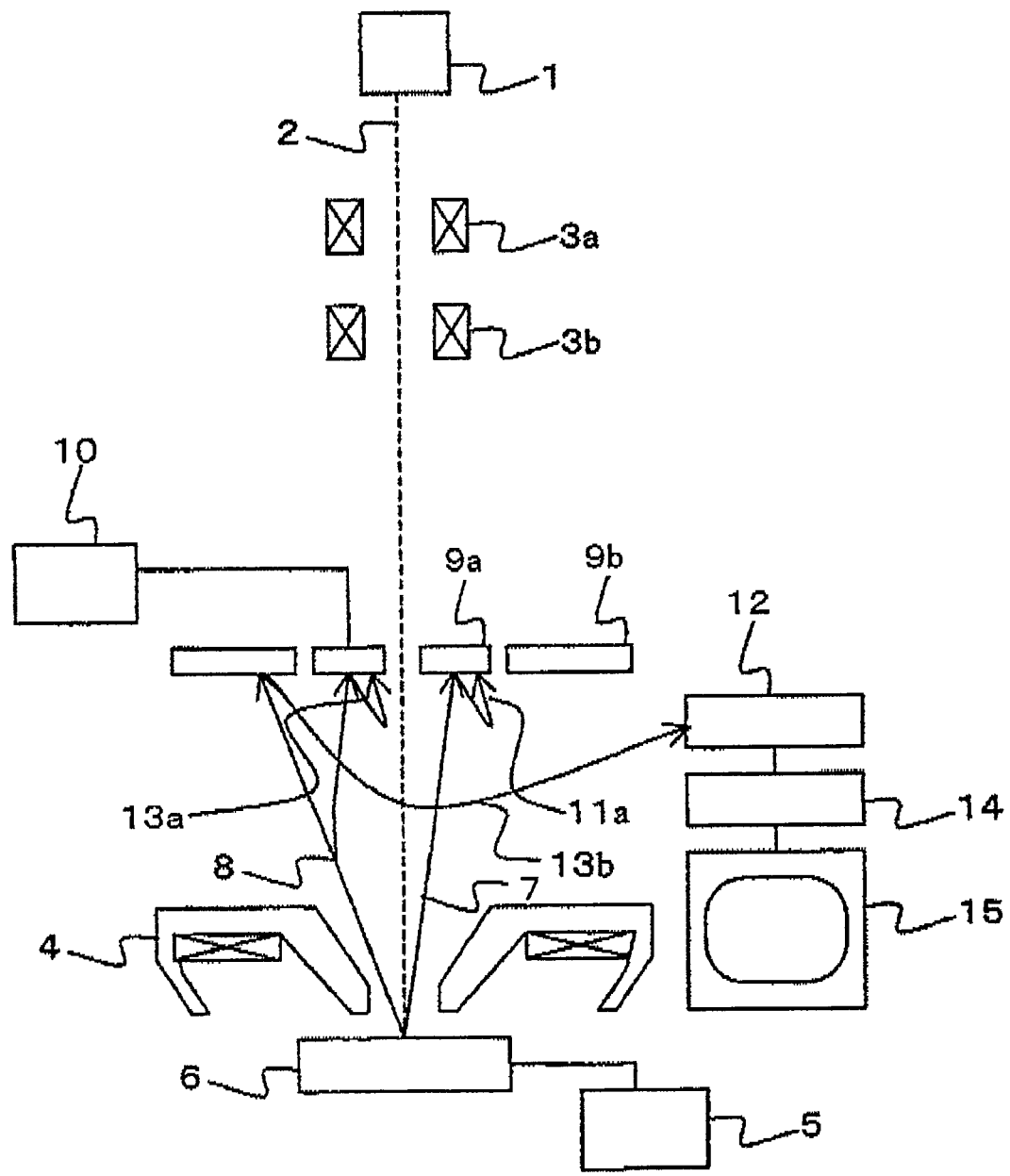
FIG. 2 is a schematic diagram for explaining a scanning electron microscope which selectively detects backscattered electrons.

On the other hand, when an image is intended to be obtained by use of only the reflected electrons, a positive potential of approximately +10V is supplied to the inner annular part 9a from the voltage applying mechanism 10. FIG. 2 shows how the scanning electron microscope of the present example works. The secondary electrons 7 collide against the inner annular part 9a as in the case of the secondary electrons 7 colliding against the inner annular part 9a when the positive voltage is applied thereto. Because the inner annular part 9a and the components (not illustrated) in its vicinity are set at the ground potential, the secondary electrons 11a are repulsed back to the inner annular part 9a by the electric field, and are absorbed in the inner annular part 9a, even though the secondary electrons 11a are once emitted from the surface of the inner annular part 9a.

Most of the reflected electrons 8 collide against the outer annular part 9b whereas the rest of the reflected electrons 8 collide against the inner annular part 9a, as in the case shown in FIG. 1. Secondary electrons 13 are regenerated in each surface of the inner annular part 9a and the outer annular part 9b due to the energy of the reflected electrons colliding against the two annular parts, and are thus emitted from the two annular parts. Out of the secondary electrons 13 thus generated, secondary electrons 13a generated in the inner annular part 9a are repulsed back to the inner annular part 9a by the electric field, and are absorbed in the inner annular part 9a, even though the secondary electrons 13a are once emitted from the surface of the inner annular part 9a.

Out of the secondary electrons 13 thus generated, secondary electrons 13b generated in the outer annular part 9b are attracted by the electric field caused due to the voltage applied to the front of the secondary electron detector 12, and thus reach the secondary electron detector 12. Thereby, the secondary electron detector 12 detects only the signal due to the reflected electrons 8. The signal detected by the secondary electron detector 12 and signals from the other detectors (not illustrated) are selected, combined and colored by the signal processing means 14, followed by a display on the display device 15.

In short, in the case where the positive potential is supplied to the inner annular part 9a, the information on the reflected electrons 8 only is acquired. Specifically, the change of the voltage applied to the inner annular part 9a enables the scanning electron microscope to effectively change the inner diameter of its detection section, and to thereby detect the secondary electrons and/or the reflected electrons selectively.

In the case of the examples of the scanning electron microscope shown in FIGS. 1 and 2, the lower surfaces respectively of the inner annular part 9a and the outer annular part 9b are flat and in the same plane. However, the scanning electron microscope may have a configuration in which the lower surface of the inner annular part 9a is positioned higher than that of the outer annular part 9b.

The secondary electrons 7 and the reflected electrons 8 are accelerated by the electric field for decelerating the primary beam of electrons 2. For this reason, the secondary electrons 7 and the reflected electrons 8 each have an energy of more than 1500 eV at the position of the detection electrode 9. When the secondary electrons 7 and the reflected electrons 8 collide against the inner annular part 9a, not only secondary electrons 11 and 13 but also reflected electrons 19 are regenerated with a specific ratio.

The reflected electrons 19 travel straight in the electric field which is caused due to the voltage of approximately +10V applied to the inner annular part 9a, because the reflected electrons 19 do not change their trajectories in the electric field. The scanning electron microscope of the present example has a physical obstacle in the path from the position on the inner annular part 9a, where the reflected electrons 19 are generated, to the secondary electron detector 12. This enables the scanning electron microscope to check the detection of the reflected electrons 19, and to thereby detect the secondary electrodes and/or the reflected electrons selectively with higher precision.

Figure 3:
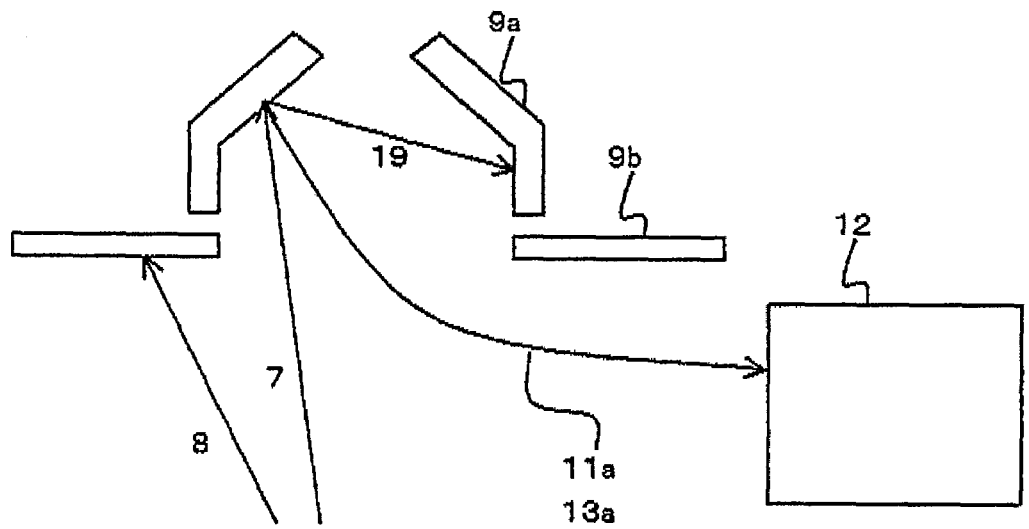
FIG. 3 is a diagram for explaining an example of how a depth is provided to an inner annular part of a detection electrode.

FIG. 3 shows bow the scanning electron microscope of the present example operates in the vicinity of the detection electrode 9. It should be noted that, when the negative voltage or the ground potential is applied to the inner annular part 9a, the trajectories of the secondary electrons 11 and 13 regenerated by the electric field caused due to the applied voltage are guided to the secondary electron detector 12, and the secondary electrons are detected without any trouble.

Unlike the examples of the scanning electron microscope shown in FIGS. 1 and 2, the example thereof shown in FIG. 3 is capable of preventing electrons to pass an interstice between the inner annular part 9a and the outer annular part 9b, and of maintaining the high efficiency with which the SEs are detected, because the inner annular part 9a has a sidewall, even though the inner annular part 9a and the outer annular part 9b are not evened off at the same height.

When the scanning electron microscope does not use the deceleration method, no velocity which the secondary electrons 7 and the reflected electrons 8 would otherwise receive in the direction of the optical axis of the beam of electrons through their acceleration by the electric field is added to the velocity of each of the secondary electrons 7 and the reflected electrons 8. As a result, the secondary electrode 7 and the reflected electrons 8 travel in their trajectories different from the trajectories which have been described with reference to the illustrations in FIGS. 1 and 2. This makes the scanning electron microscope incapable of selectively detecting the second electrons and/or the reflected electron by applying the voltage to the inner annular part 9a.

With this taken into consideration, the apparatus may be set up in order that, only when the apparatus uses the deceleration method, the positive voltage is capable of being applied to the inner annular part 9a. Otherwise, the apparatus may be designed in order that when the apparatus uses the deceleration method, the positive voltage can be automatically applied to the inner annular part 9a. Furthermore, in a case where the voltage applied to the sample by the decelerating-voltage applying voltage supply 5 is low, it is likely that the trajectories of the secondary electrons may be insufficiently separated from the trajectories of the reflected electrons, and that the scanning electron microscope is accordingly incapable of selectively detecting the secondary electrons and/or the reflected electrons with efficiency.

For this reason, the apparatus may be set up in order that, when the voltage applied by the decelerating-voltage applying voltage supply 5 becomes equal to or higher than a predetermined value, a control can be made so that the decelerating-voltage applying voltage supply 5 is capable of applying the positive voltage to the inner annular part 9a of the detection electrode. Otherwise, such a control may be made by a control device (not illustrated). In a case where some change of image or a predetermined image condition is detected, the scanning electron microscope may be designed to make an automatic control for switching between the detection of the BSEs and the detection of the SEs. For example, in a case where the amount of signal in the SEs is excessive so that the image looks whitish, or in a case where the amount of signal in the BSEs is sparse so that the image looks dark, a control may be made for switching from one to the other of the detection means depending on the detected condition.

Figure 4:
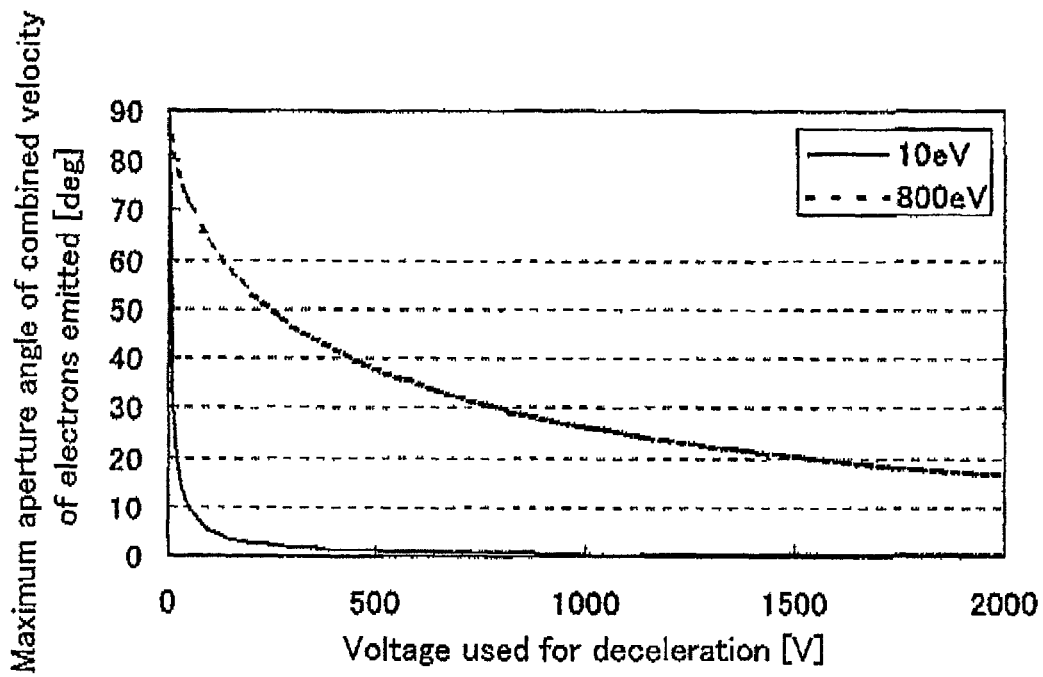
FIG. 4 is a diagram for explaining a relationship between a voltage applied to a sample by use of a deceleration method and a maximum aperture angle of electrons emitted from the sample.

As a desirable example, it is rational that the voltage of the decelerating-voltage applying voltage supply 5 to be used for setting up the apparatus should be set equal to or less than 50V. FIG. 4 shows the maximum aperture angle of the secondary electrons and the reflected electrons whose respective velocities include the added velocities as a result of the deceleration method. The decelerating voltage of 50V compresses the aperture angle of the secondary electrons having a kinetic energy of 10 eV to 10 degrees, and the aperture angle of the reflected electrons having a kinetic energy of 800 eV to 70 degrees. This angle difference is large enough for the scanning electron microscope according to the present invention to distinguish between the secondary electrons and the reflected electrodes.

Under the foregoing conditions, the scanning electron microscope is capable of distinguish between the secondary electrons and the reflected electrons by providing the outer annular part 9b with an opening which electrons having a maximum aperture angle equal to or less than 10 degrees are selectively allowed to pass, and concurrently by providing the inner annular part 9a inside or above the opening.

Figure 5:
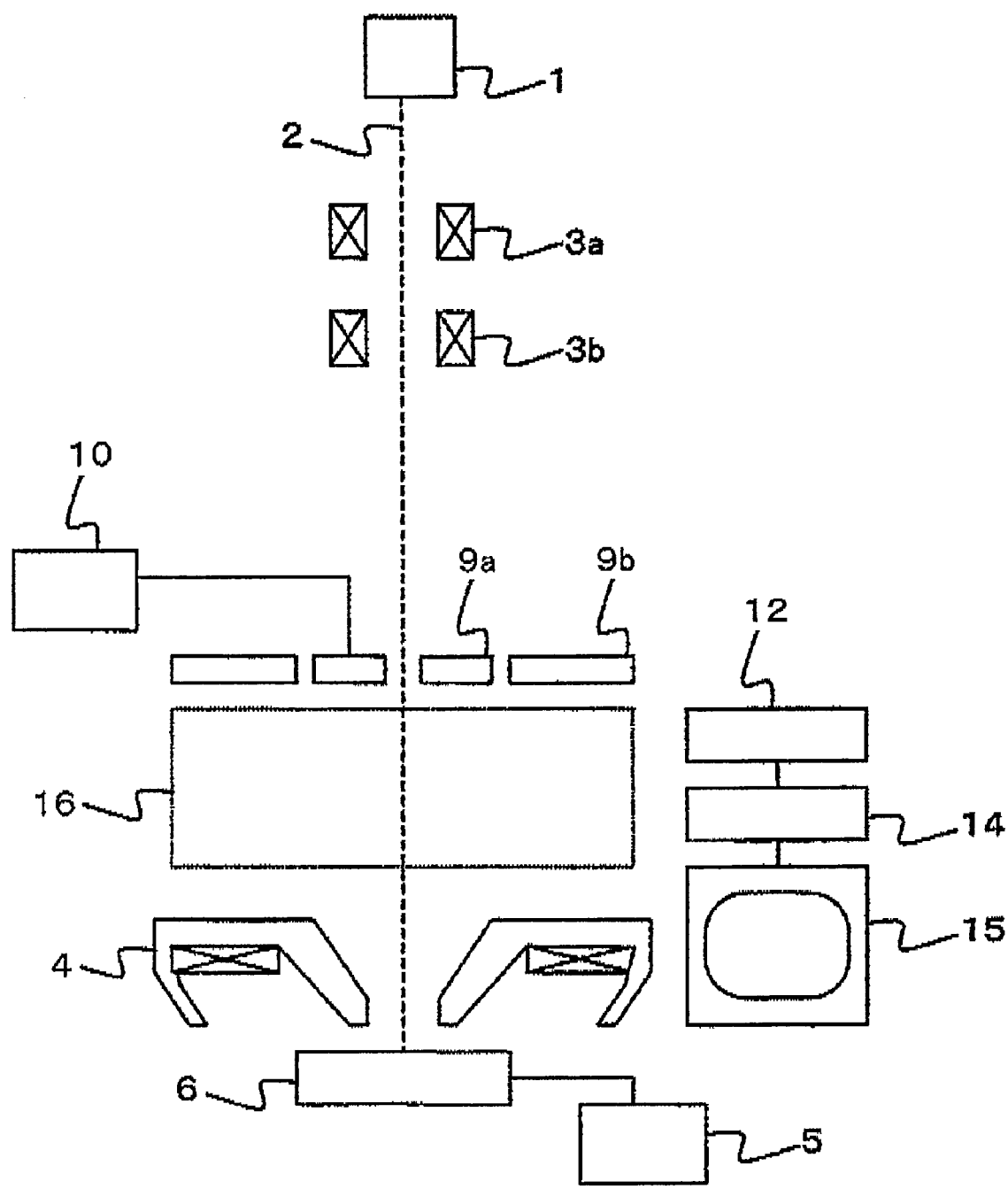
FIG. 5 is a schematic diagram of a scanning electron microscope including an ExB (electron-beam) deflector.

The examples of the scanning electron microscope shown in FIGS. 1 and 2 cause the secondary electrons 11 and 13 regenerated on the detection electrode 9 to be attracted only by the electric field caused due to the voltage applied to the front of the secondary electrode detector 12. The configuration for this attraction may further include the E×B deflector (orthogonal electric field generator) 16 in a position including the optical axis of the beam of electrons. FIG. 5 shows a configuration adopted for this case. In a case where the E×B deflector is used, the scanning electron microscope is capable of forcefully attract the regenerated secondary electrons 11 and 13 without affecting the trajectory of the primary beams of electrons 2. This orthogonal electric field generator is disclosed, for example, in Japanese Patent Application Laid-open Publication No. Hei 9-171791 (Patent Document 6).

Figure 6:
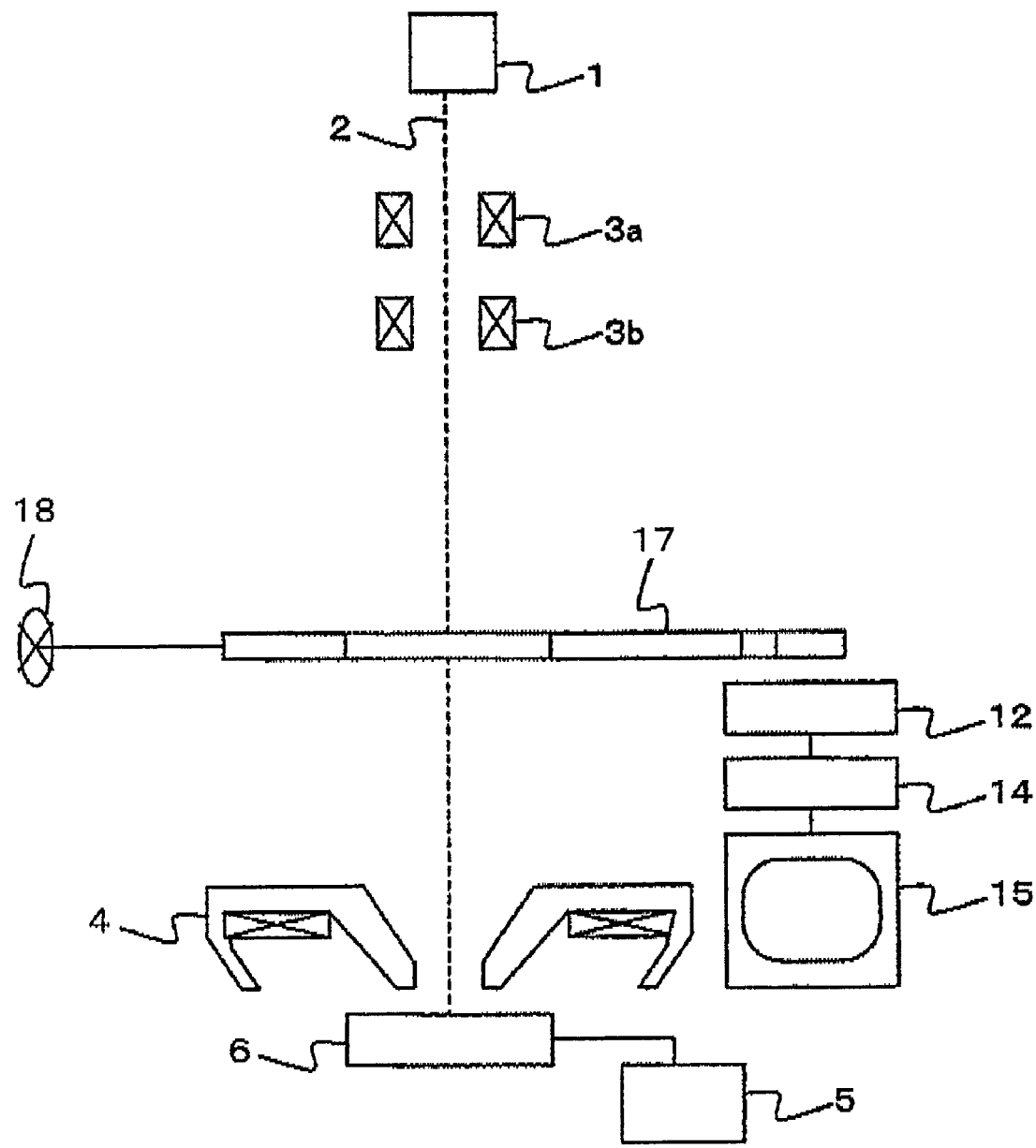
FIG. 6 is a schematic diagram of a scanning electron microscope including a movable detection plate.

FIG. 6 is a schematic diagram showing an example of a scanning electro microscope which mechanically changes the inner diameter of the detection section. In lieu of the detection electrode 9, a movable detection plate 17 is arranged at the same position as the detection electrode 9 is arranged.

In a case where hole with a small diameter is placed for the optical axis of the primary beam of electrons 2 to pass the hole, both the secondary electrons 7 and the reflected electrons 8, which are generated when the primary beam of electrons 2 is irradiated on the sample 6, collide against the movable detection plate 17, and the secondary electrons 11 and 13 are thus regenerated. The secondary electrons thus regenerated are attracted by the electric field caused due to the voltage applied to the front of the secondary electron detector 12, and hence reach the secondary electron detector 12.

Thereby, the secondary electron detector 12 detects a signal due to the secondary electrons and a signal due to the reflected electrons. The signals detected by the secondary electron detector 12 and signals from the other detectors (not illustrated) may be selected, combined and colored by signal processing means 14, followed by a display on the display device 15.

In the case where a hole with a large diameter in the movable detection plate 17 is placed for the optical axis of the primary beam of electrons 2 to pass the hole, through operating a moving mechanism 18, the reflected electrons, which are generated when the primary beam of electrons 2 is irradiated on the sample 6, selectively collide against the movable detection plate 17, and secondary electrons are thus regenerated. The secondary electrons thus regenerated are attracted by the electric field caused due to the voltage applied to the front of the secondary electrode detector 12, and hence reach the secondary electron detector 12.

Thereby, the secondary electrode detector 12 detects a signal due to the reflected electrons. The signal detected by the secondary electron detector 12 and signals from the other detectors (not illustrated) are selected, combined and colored by signal processing means 14, followed by a display on the display device 15.

In other words, the scanning electron microscope is capable of selectively detecting the secondary electrons and/or the reflected electrons by changing the position of the movable detection plate 17, and concurrently by mechanically changing the inner diameter.

Like the example of the scanning electron microscope shown in FIG. 3, the present example thereof may further include the E×B deflector (orthogonal electric field generator) 16 for the purpose of forcefully attracting the regenerated secondary electrons.

Figure 7:
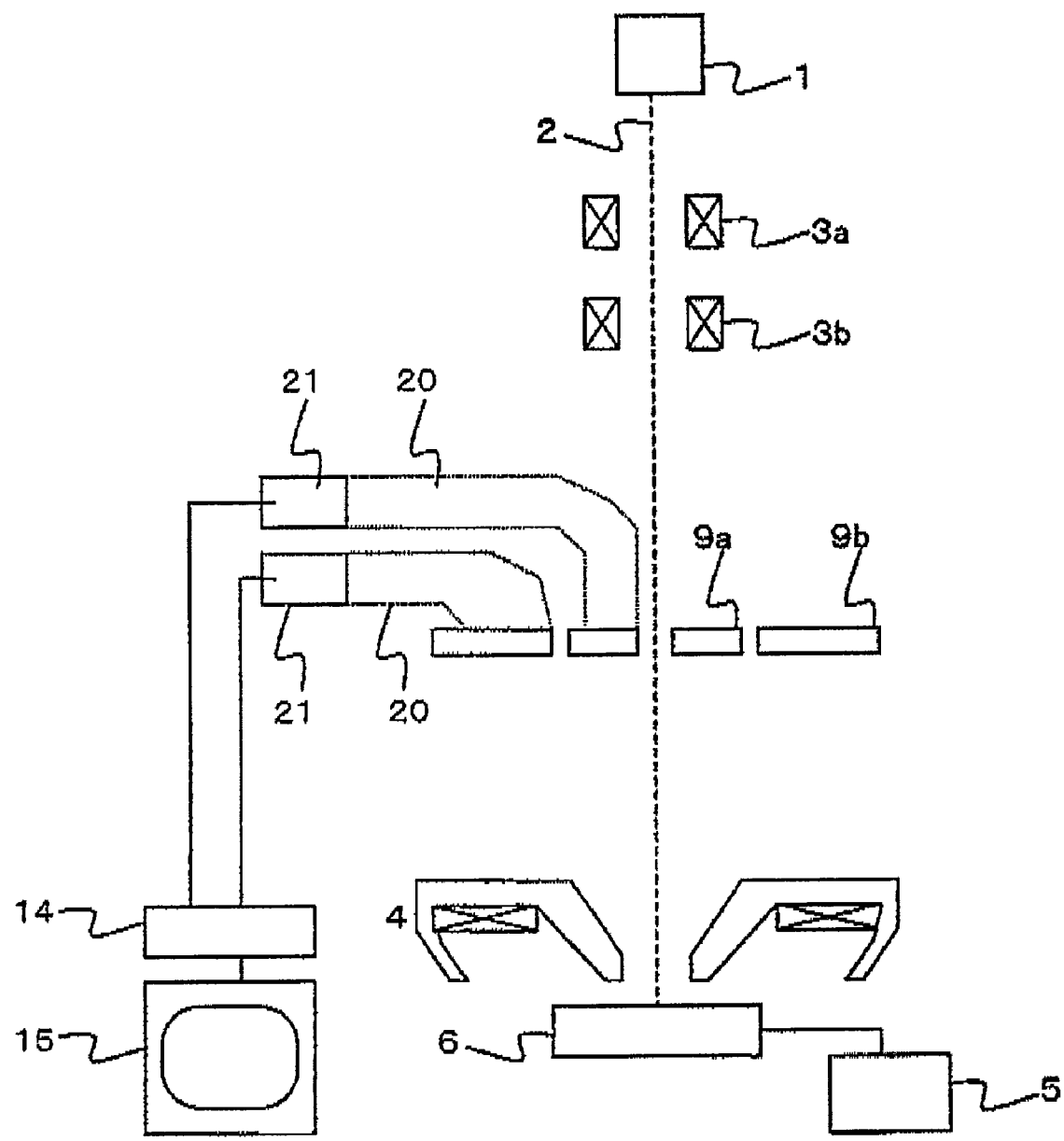
FIG. 7 is a schematic diagram of a scanning electron microscope including a scintillator as a detector.

FIG. 7 is a schematic diagram showing an example of a scanning electron microscope which is configured by including an inner and outer annular detectors. In lieu of the detection electrode 9 in the example thereof shown in FIGS. 1 and 2, scintillators 19 are arranged at the same position as the detection electrode 9 is arranged. An inner scintillator 19a and an outer scintillator 19b are blocked from light separately in order that the two scintillators should be optically independent of each other. The secondary electrons 7 and the reflected electron 8 which are generated when the primary beam of electrons is irradiated on the sample 6 are made incident on the inner scintillator 19a and the outer scintillator 19b, respectively. Thereby, a luminous phenomenon takes place in the two scintillators.

Light generated in the scintillators 19 is guided to photomultipliers 21 connected to the scintillators 19 with light guides 20, respectively. The light generated in each of the scintillators is converted to an electric signal. The signals detected by the respective photomultipliers 21 and signals from the other detectors (not illustrated) are selected, combined and colored by signal processing means 14, followed by a display on the display device 15. A signal chiefly due to the secondary electrons 7 is obtained from the inner scintillator 19a, whereas a signal chiefly due to the reflected electrons 8 is obtained from the outer scintillator 19b. Thereby, the scanning electron microscope is capable of selectively detecting the secondary electrons and/or the reflected electrons.

The detector of the present example of the scanning electron microscope is configured of the scintillators. Instead, the detector may be configured of annular semiconductor detectors, or multi-channel plates.

As described above, the apparatus according to the example of the present invention is capable of selectively detecting the secondary electrons and the reflected electrons even under the condition that the decelerating method is used, and that the irradiation voltage is low.

Figure 8:
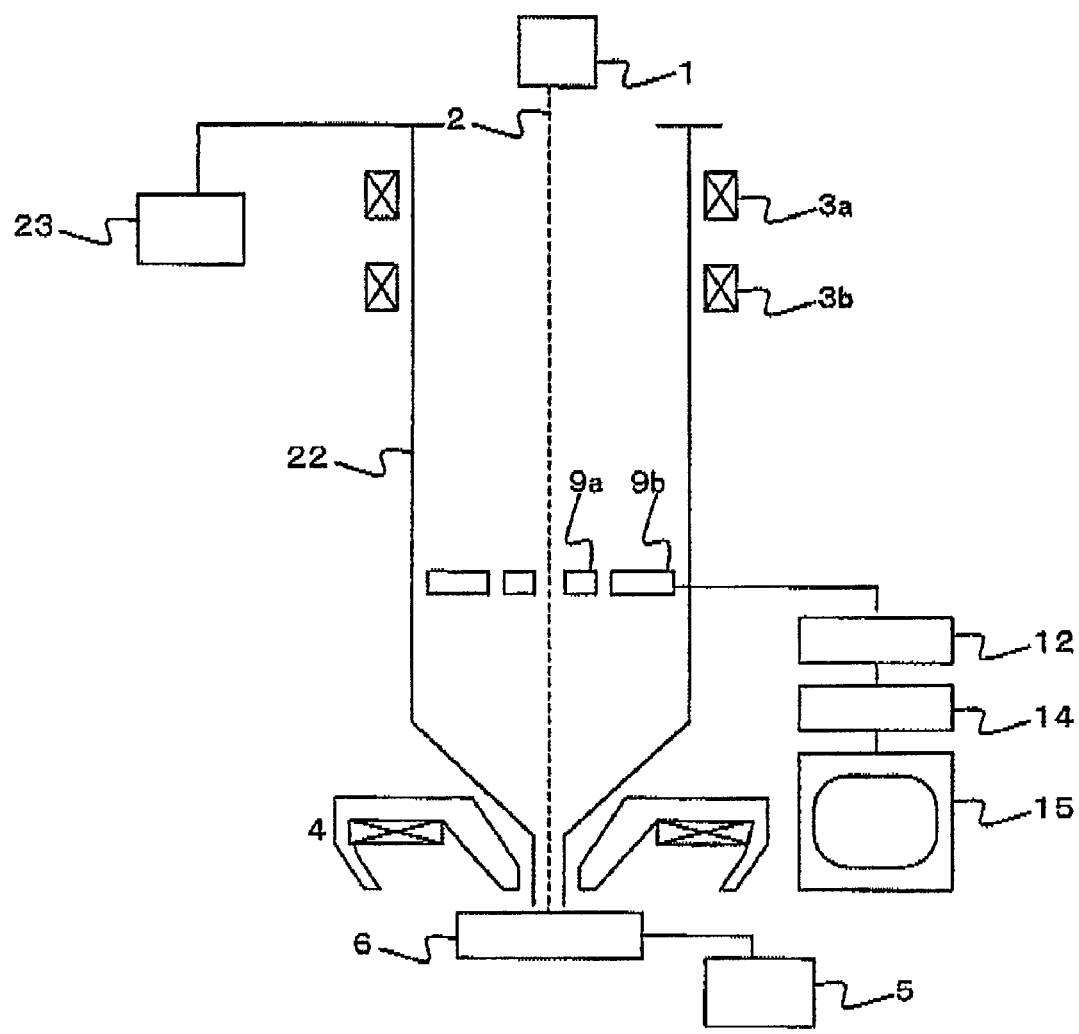
FIG. 8 is a schematic diagram of a scanning electron microscope using an accelerating cylinder as decelerating-electric-field forming means.

FIG. 8 is a diagram for explaining another example of the present invention. The present example of the scanning electron microscope uses an acceleration cylinder 22 which is formed along the optical axis of the beam of electrons as the decelerating-electric-field forming means. A positive voltage is applied to the acceleration cylinder 22, and thus the beam of electrons drawn out of the source of electrons 1 is accelerated by an accelerating-voltage applying voltage supply 23. The accelerated beam of electrons 2 is decelerated by the difference in potential between the acceleration cylinder 23 and the sample 6, and thus reaches the sample 6.

Even though the scanning electron microscope is configured in the foregoing manner, a decelerating electric field is formed between the acceleration cylinder 23 and the sample 6. As a result, the trajectories of the backscattered electrons are different from the trajectories of the secondary electrons, like the electrons in the foregoing examples of the scanning electron microscope. In other words, the secondary electrons collide against the inner annular part 9a whereas the backscattered electrons collide against the outer annular part 9. For this reason, the scanning electrode microscope is capable of selectively detecting the secondary electrons and the backscattered electrons by appropriately arranging the inner annular part 9a and the outer annular part 9b.

What is claimed is:

1. A method of measuring or observing a sample by use of a scanning electron microscope which irradiates a beam of electrons on the sample while applying a negative voltage to the sample, and hence detects electrons emitted from a spot on the sample where the beam of electrons is irradiated, wherein backscattered electrons are detected by a detector, the backscattered electrons being emitted from the sample and subsequently traveling outside trajectories of secondary electrons when viewed from an optical axis of the beam of electrons, the secondary electrons being accelerated by an electric field formed on a basis of a negative voltage applied to the sample, the detector including a part for receiving electrons in the trajectories of the backscattered electrons but outside the trajectories of the secondary electrons accelerated by the electric field.

2. The method of measuring or observing a sample as recited in claim 1, wherein the detector includes a part for receiving secondary electrons in the trajectories of the secondary electrons thus accelerated.

3. A scanning electron microscope, which includes: a source of electrons; an objective lens for focusing a beam of electrons emitted from the source of electrons; and a negative-voltage applying voltage supply for applying a negative voltage to a sample, the scanning electron microscope comprising a detector including a part for receiving backscattered electrons emitted from the sample, the detector being provided in trajectories of the backscattered electrons, and the detector being positioned outside trajectories of secondary electrons when viewed from an optical axis of the beam of electrons, the secondary electrons being accelerated by an electric field formed on a basis of the negative voltage which is applied to the sample by the negative-voltage applying voltage supply.

4. The scanning electrode microscope as recited in claim 3, further comprising a part for receiving the secondary electrons thus accelerated, the part being positioned closer to the optical axis of the beam of electrons than the part for receiving the backscattered electrons.

5. The scanning electron microscope as recited in claim 4, wherein the part for receiving the backscattered electrodes and the part for receiving the secondary electrons are electrically insulated from each other.

6. The scanning electron microscope as recited in claim 4, wherein a voltage applying voltage supply is connected to the part for receiving the secondary electrons.

7. The scanning electron microscope as recited in claim 4, wherein the part for receiving the backscattered electrodes and the part for receiving the secondary electrons are detection surfaces of the detector.

8. The scanning electron microscope as recited in claim 4, wherein the part for receiving the backscattered electrodes and the part for receiving the secondary electrons constitute a secondary electron conversion electrode for generating secondary electrons by the collision of electrons.

9. The scanning electron microscope as recited in claim 3, wherein the part for receiving the backscattered electrons includes an opening which the beam of electrons is allowed to pass.

10. The scanning electron microscope as recited in claim 9, further comprising a moving mechanism for moving the position of the opening which the beam of electrons is allowed to pass between inside and outside of the optical axis of the beam of electrons.

11. The scanning electron microscope as recited in claim 9, wherein the moving mechanism is configured in order to switch between the opening made in the part for receiving the backscattered electrons and an opening made in the part for receiving the secondary electrodes.

12. The scanning electron microscope as recited in claim 9, wherein the opening made in the part for receiving the backscattered electrons is larger than the opening made in the part for receiving the secondary electrons.

\* \* \* \* \*